United States Patent [19]

Takahashi et al.

[11] Patent Number: 5,001,053
[45] Date of Patent: Mar. 19, 1991

[54] METHOD AND APPARATUS FOR MEASURING THE PRODUCT OF AN ANTIGEN-ANTIBODY REACTION

[75] Inventors: Masao Takahashi; Toshihiko Tazawa, both of Tokyo, Japan

[73] Assignee: Nihon Kohden Corporation, Tokyo, Japan

[21] Appl. No.: 243,296

[22] Filed: Sep. 12, 1988

[51] Int. Cl.⁵ .......................... G01N 33/543
[52] U.S. Cl. .......................... 435/7.1; 435/4; 435/810; 436/510; 436/518; 436/806; 422/68.1; 422/82.01
[58] Field of Search ............. 435/7.81, 4; 436/501, 436/518, 806; 422/68, 68.1, 82.01

[56] References Cited

U.S. PATENT DOCUMENTS

| 4,236,893 | 12/1980 | Rice .......................... 436/513 |
| 4,242,096 | 12/1980 | Oliveira et al. ............. 436/513 |
| 4,537,861 | 8/1985 | Elings et al. ............... 436/518 |

FOREIGN PATENT DOCUMENTS 8002201  10/1980  World Int. Prop. O. .

OTHER PUBLICATIONS

Patent Abstracts of Japan, 62-150148, Yoshikawa et al., Abs. vol. 11, No. 383; Published 12/15/1987.

Primary Examiner—Esther L. Kepplinger
Assistant Examiner—Carol A. Spiegel
Attorney, Agent, or Firm—Hoffmann & Baron

[57] ABSTRACT

A method and an apparatus for detecting antigen-antibody reaction are disclosed in which a predetermined antigen or antibody is made to attach to the surface of an oscillator and the oscillator is immersed in the specimen blood so as to cause antigen-antibody reaction on the surface thereof. The oscillator is then made to oscillate and the amount of antibody or antigen attaching to the surface of the oscillator is determined in accordance with the data concerning the oscillation of the oscillator.

6 Claims, 5 Drawing Sheets

METHOD AND APPARATUS FOR MEASURING THE PRODUCT OF AN ANTIGEN-ANTIBODY REACTION

BACKGROUND OF THE INVENTION

The present invention relates to a method of and apparatus for detecting antigen-antibody reaction, suitable for use in immunological test.

It is well known, that when foreign or potentially dangerous substances, particularly disease producing microorganisms (i.e. antingens), are in or introduced into the body, an "immune response" or reaction naturally occurs. This response involves the production of proteins known as "antibodies", which react with the antigens to render them harmless. Such production is achieved by specialized white blood cells (i.e. lymphocytes). Antibody production is one aspect of the immune response and is stimulated by antigens such as invading bacteria, foreign red blood cells, inhaled pollen grains or dust, and foreign tissue grafts. Notably, antibody-antigen reactions are highly specific.

Thus, it is important to be able to determine in some qualitative as well as quantitative manner, a person's immunity to certain "antigens". The way that a person's immune system is tested is by immunological testing.

Hitherto, there have been proposed a variety of immunological test methods, which are summarized below.

(a) Precipitation Method

This method can be broadly sorted into two types, (1) qualitative methods such as ring test, capillary test, tube test and immuno diffusion test, and (2) quantitative methods such as quantitative precipitation method, laser nephelometry and quantitative immuno diffusion method. The precipitation method, which is the most basic and conventional method, requires a long reaction time, as well as observation and evaluation by an expert. It is therefore difficult to automate this method. In addition, this method can be applied only to large protein antigens.

(b) Hemolytic Plaque Assay

This method involves conducting qualitative and quantitative analysis by effecting hemolysis and cell lysis of a combinative product of cellular antigen and antibody, e.g., red corpuscle and bacterium, by making use of a complement contained in fresh blood. This method enables an examination with a high level of sensitivity but most steps of the process rely upon expensive reagent and laborious manual work. In addition, the final determination has to be done through microscopic study or use of a photo-absorption technique. For these reasons, this method also is unsuitable for automation.

(c) Agglutination Technique

This technique includes various methods such as red corpuscle/bacterium agglutination, anti-globulin test (Coombs test), passive hemolytic coagulation assay (PHA, HA) and immuno adherence assay (IA). According to this technique, cellular antigen is caused to agglutinate and precipitate for observation and determination, by bridge formation effected by means of an antibody. In case of a large protein antigen, the large protein antigen is adsorbed by a particle substance and subjected to combinative reaction so as to be agglutinated and precipitated to enable observation and determination. This technique offers a higher sensitivity than the precipitation method and, therefore, is most frequently used in the detection of trace amounts of antibodies, as well as in the quantitative analysis of trace amounts of cellular antigens and large protein antigens. Unfortunately, however, this technique relies mostly upon manual procedures and requires the time-consuming work of an expert.

(d) Passive Cutaneous Anaphylaxis Method (PCA) Method

According to this method, an antibody is injected cutaneously into normal living body to realize an indicated state of the cutaneous cells. Then, the corresponding antigen and dye are injected by intravenous injection, thereby enabling observation of coloring state of the indicated state at the epidermis. This technique is superior insofar as antibodies such as IgG and IgE are concerned, and exhibit a high sensitivity. Unfortunately, however, this technique is not suitable for clinical use because it necessitates animals such as rats and mice.

(e) Labelled Antibody Method

This method includes immuno fluorescence technique and enzyme immuno assay technique. According to this method, an antibody is labelled and the examination is conducted by making use of the specific affinity of the antigen-antibody reaction. This method enables a quantitative analysis of a trace amount of antigen substance. On the other hand, this technique requires time-consuming, manual work for the separation and refining of the antigen substance, and requires an expensive photometer having a high sensitivity.

Thus, all the immunological testing methods proposed heretofore are still unsatisfactory in that they require many biochemical processes necessitating time-consuming preparatory processes and laborious manual procedures, as well as a variety of expensive reagents and measuring instruments.

SUMMARY OF THE INVENTION

Accordingly, an object of the present invention is to provide a method of and an apparatus for detecting antigen-antibody reaction which enable even those who do not have a high degree of skill to conduct immunological tests in a short time, thereby overcoming the above-described problems of the prior art.

According to the present invention, an antigen or an antibody is fixed to the surface of an oscillator and the oscillator is immersed in a sample blood so that antigen-antibody reaction takes place on the surface of the oscillator and the product of the reaction adheres to the oscillator. Then, the oscillator is caused to vibrate so that the amount of the antibody or antigen adhering to the oscillator is known from the vibration data of the oscillator.

The present invention, therefore, makes it possible to measure very easily and promptly the amount of antibody (or antigen) contained in the blood. Thus, the present invention provides a remarkable effect in that the human labor, as well as reagents and instruments, can greatly be saved because any preparation of blood is almost unnecessary and because complicated physical and chemical processes which heretofore have been necessary can be eliminated. In addition, the invention enables even those who do not have a high degree of skill to conduct immunological test so that clinical immunological testing can find a wide-spread use.

DESCRIPTION OF THE PREFERRED EMBODIMENT

Figure 1:
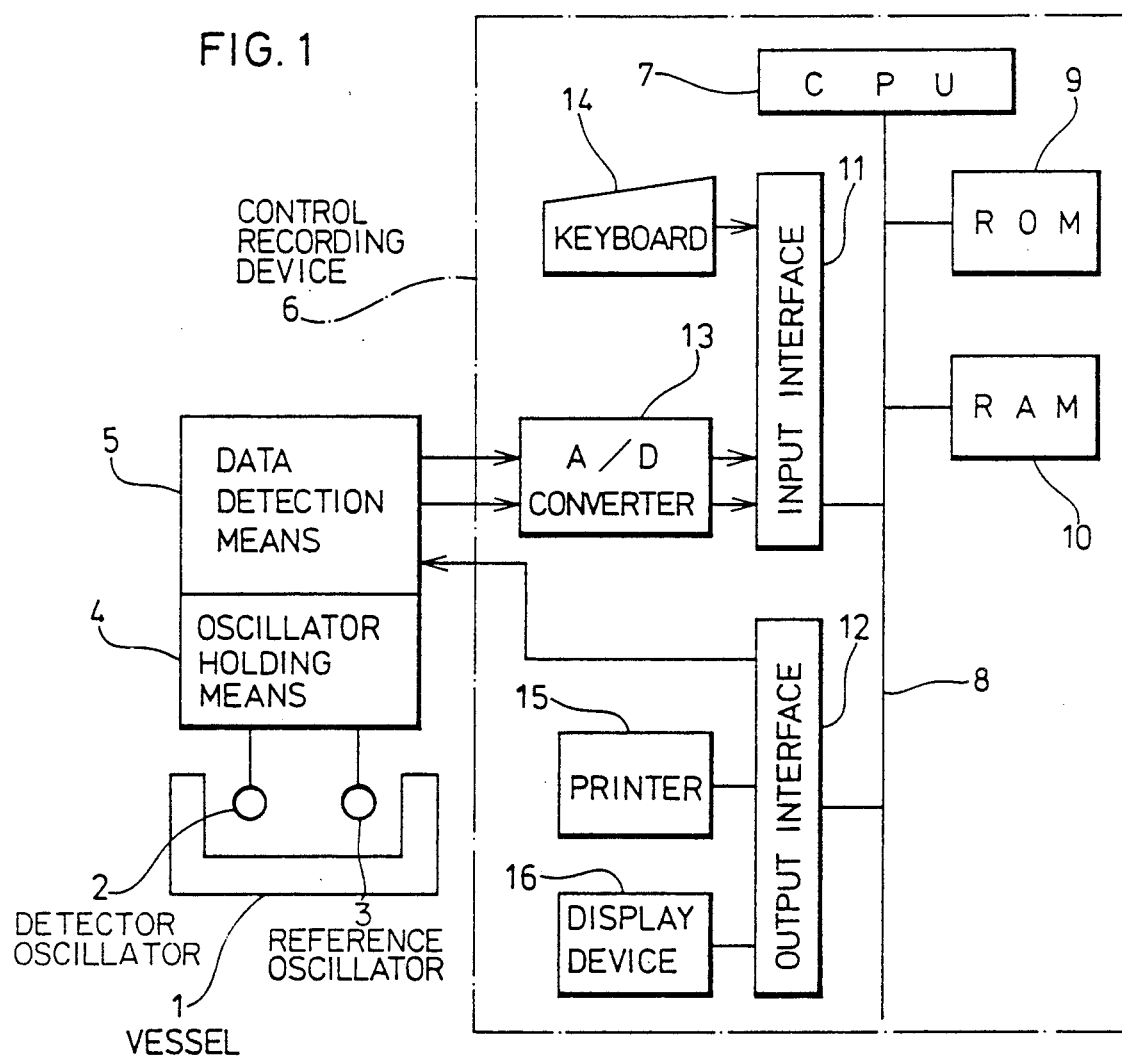
FIG. 1 is a block diagram of an apparatus to which the present invention is applied.

A description will be given of the principle of an embodiment of the present invention.

When a resistance proportional to velocity is added to a harmonic oscillator, the oscillation thereof is attenuated and stopped in a definite time. Representing the instant position of the oscillator by x, the velocity is expressed by $dx/dt$. The direction in which the resistance R acts is opposite to the direction of the velocity $dx/dt$. The resistance can be expressed as follows:

$$R = -2km(dx/dt)$$

where, m represents the mass of the oscillator, while k ($>0$) represents the proportion constant.

Then, the following equation of motion is established with respect to the oscillator:

$$m(d^2x/dt^2) = -mw^2x - 2mk \cdot (dx/dt) \quad (1)$$

where w is the angular frequency of oscillation of the harmonic oscillator.

The following equation (2) is derived from the equation (1):

$$(d^2x/dt^2) + 2k(dx/dt) + w^2x = 0 \quad (2)$$

The condition of $k^2 - w^2 < 0$ is met, when the resistance is very small. In such a case, the equation (2) is solved as follows, on condition of $w^2 - k^2 = w'^2$:

$$x = ae^{-kt} \cos(w't + \beta) \quad (3)$$

where, $\alpha$ and $\beta$ are constants.

The equation (3) represents that the oscillation is progressively attenuated in a region which is defined between two curves: namely, $x = ae^{-kt}$ and $x = -ae^{-kt}$.

The time T required for the amplitude of oscillation of the oscillator to change from a predetermined value $x_0$ to another predetermined value $x_n$ where $(x_0 > x_n)$, is given as follows:

$$T = t_n - t_0 \quad (4)$$

where, $t_0$ and $t_n$ represent the moments at which the amplitudes are $x_0$ and $x_n$, respectively.

The values $x_0$ and $x_n$ are on an envelope curve $x = ae^{-kt}$, particularly in the region of $x > 0$, so that they are expressed as follows, respectively:

$$x_n = ae^{-kt_n} \quad (5)$$

$$x_0 = ae^{-kt_0} \quad (6)$$

The following equations are obtained from logarithmic expressions and modifications of the equations (5) and (6):

$$t_n = (-1/k) \cdot \ln(x_n/a) \quad (7)$$

$$t_0 = (-1/k) \cdot \ln(x_0/a) \quad (8)$$

The following equation is obtained by substituting the equations (7) and (8) to the equation (4):

$$T = (-1/k) \cdot \ln(x_n/x_0) \quad (9)$$

Representing the radius of the oscillator by a, the mass of the oscillator by m and viscosity of the fluid contacting the oscillator by $\eta$, the proportion constant K is expresed as follows:

$$K = 3\pi a\eta/m \quad (10)$$

The equation (10) can be modified as follows, by representing the density of the oscillator by p:

$$K = 3\pi a\eta / \{(4/3\pi) a^3 \cdot p\} \quad (11)$$
$$= 9\eta/(4a^2 p)$$

The following equation is obtained by substituting the equation (11) for the equation (9):

$$|T| = \{4a^2 p/(9\eta)\} \cdot \ln(x_n/x_0) \quad (12)$$

As will be seen from the equation (12), since the factors p, $\eta$, $x_n$ and $x_0$ are constants, the attenuation time T is proportional to the square of the radius "a" of the oscillator. It is, therefore, possible to determine the radius, a, and the mass "m" of the oscillator can be determined from the value of the radius "a".

The embodiment of the invention is based upon this principle.

Figure 3:
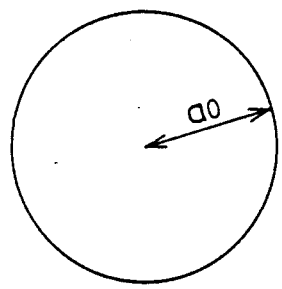
FIG. 3 is an illustration of a change in radius of the oscillator.
Figure 3:
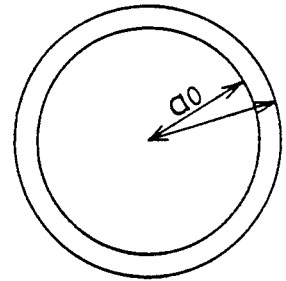

A predetermined antigen or an antibody is fixed to the surface of an oscillator having a radius $a_0$ as shown in FIG. 3(i), and the oscillator is immersed in a blood extracted from a patient so that an antibody or an antigen corresponding to the antigen or antibody on the oscillator attaches to the surface of the oscillator to increase the radius to $a_1$ as shown in FIG. 3(ii). Then, attenuation of oscillation of the oscillator is commenced, and the attenuation time $T_1$ is measured.

This measured value of the attenuation time $T_1$ should satisfy the following condition derived from the equation (12):

$$|T_1| = \{4a_1^2 p/(9\eta)\} \cdot \ln(x_n/x_0)$$

The radius $a_1$ can therefore be determined, from which the increment $\Delta V$ is determined as follows:

$$\Delta V = 4/3\pi(a_1^3 - a_0^3) \quad (14)$$

Representing the mean density of the product of the antigen-antibody reaction by p', the increment $\Delta m$ of the mass is given as follows:

$$\Delta m = 4/3\pi(a_1^3 - a_0^3)p' \quad (15)$$

It is thus possible to determine the mass of the product of the antigen-antibody reaction.

In the method as described, the oscillation is attenuated and the mass of the product of the antigen-antibody reaction is determined from the relationship existing between the attenuation time and the radius of the oscillator. Various methods would be possible for determining the mass of the reaction product from a change in the oscillation of the oscillator. However, the method described hereinabove is preferred for the following reasons.

(1) Sensitivity Level Required in Measurement of Antigen-Antibody Reaction

Figure 4:
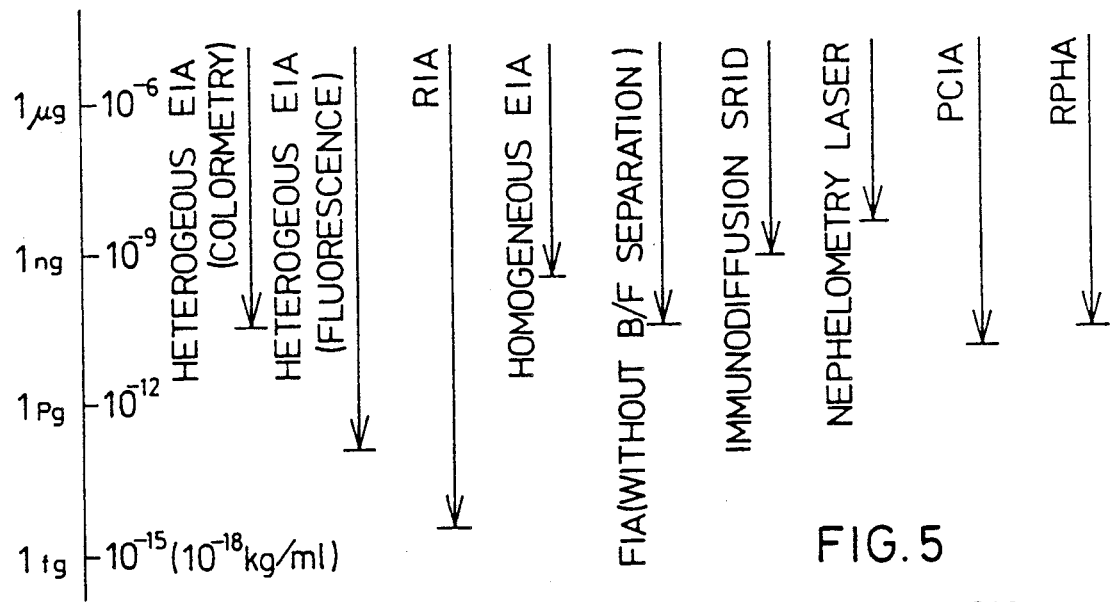
FIG. 4 is an illustration of a range of density measurable by conventional antigen-antibody reaction examination method.

FIG. 4 shows known methods and levels of sensitivity in such known methods. As will be seen from this Figure, the RIA method exhibits the highest sensitivity. More specifically, the RIA method has a sensitivity as high as $10^{-18}$ kg/m. This means that, if the method of the present invention is capable of sensing this trace amount, the method of the invention is superior to any of known methods.

(2) Relationship Between Oscillation and Mass (a) When the oscillator is a chord, the angular frequency w is expressed by the following equation:

$$w = (n\pi/L)\sqrt{T/\sigma} \quad (16)$$

where, $\sigma$ represents the density of the chord, T represents the tension in the chord and L represents the length of the chord.

(b) When the oscillator is a rod, the angular frequency w is expressed by the following equation:

$$w = (n\pi/L)\sqrt{E/\sigma} \quad (17)$$

where, $\sigma$ represents the density of the chord, E represents the Young's modulus and L represents the length of the rod.

From the equations (16) and (17), it will be clear that the frequency of oscillation of the chord or the rod is proportional to the root of the line density or solid density of the chord or the rod. When the amount of the antigen-antibody reaction product attaching to the oscillator is on the order of $10^{-18}$, the amount of change in the oscillation frequency is as small as $-1/18$ or less in terms of power, even if the change in the mass is equal to the apparent change in the volume of the oscillator. From a technical point of view, it is extremely difficult to measure such a small change in the oscillation frequency. This means that the quantitative analysis of the combinative antigen (or antibody) through measurement of change in the oscillation frequency is materially difficult to conduct.

(3) Relationship Between Period of Attenuating Oscillation and Mass

From the equation (3), the period T of the attenuating oscillation is given as follows:

$$T = 2\pi/w' = 2\pi/\sqrt{w^2 - k^2} \quad (18)$$

$$= (2\pi/w) \cdot (1/\sqrt{1 - k^2/w^2}) \quad (19)$$

The condition of $k = 3\pi a\eta/m$ is derived from the equation (10). On condition of $n = 10^{-3}$ N·sec/m², $a = 10^{-3}$ m and $m = 10^{-3}$ kg, a condition of $w^2 \gg k^2$ is met when $w^2 = 10^6$, so that $k^2/w^2$ approaches zero. The equation (19), therefore, can be rewritten as follows:

$$T = 2\pi/w \quad (20)$$

Thus, the period is the same as that obtained when the mass is in the air, and no change in the period is caused by the increment $10^{-18}$ kg of the mass.

(4) Relationship Between Change in Oscillation Amplitude and Mass

The following relationship is obtained by differentiating the formual (3) with t:

$$dx/dt = ae^{-kt}\{-k\cos(w't+\beta) - w'\sin(w't+\beta)\}$$

If the values a and b are determined to meet the conditions of $k = a \sin b$ and $w' = a \cos b$, the following condition is met:

$$x/dt = ae^{-kt}\sin(w't+\beta+b)$$

The velocity dx/dt is zero at a moment $t_n$ which meets the ocndition of $w't_n + \beta + b = n\pi$.

Thus, moments periodically appear at which the $|x|$ takes the maximum value, with a constant period which equals to the period of oscillation.

The maximum value $x_n$ obtained at the moment $t_n$ is given as follows:

$$x_n = ae^{-kt}\cos(n\pi - b)$$

The maximum value obtained at a moment $t_{n+2}$ which is one period $(2\pi/w')$ from the moment $t_n$ is expressed by $x_{n+2}$. The ratio between the maximum values $x_{n+2}$ and $x_n$ is then determined as follows:

$$\begin{aligned} x_{n+2}/x_n &= e^{-k(t_{n+2}-t_n)}\cos\{(n+2)\pi - b\}/\cos(n\pi - b) \\ &= \exp(-k'2\pi/w') \\ &= \exp(-2\pi k/\sqrt{w^2 - k^2}) \end{aligned} \quad (21)$$

Thus, the ratio is a constant value which is independent from the time. This suggests that the amplitude decreases at a constant ratio.

The logarithmic attenuation factor is derived as follows from the formula (21):

$$= -\log(x_{n+2}/x_n) = 2\pi k/\sqrt{w^2 - k^2} \quad (22)$$

Thus, the amplitude decreases by 1/e in each period. The period of attenuating oscillation is given as follows:

$$T = 2\pi/\sqrt{w^2 - k^2} = (2\pi/w)/\sqrt{1 - k^2/w^2} \quad (23)$$

Since condition of $w^2 \gg$ is met, the period T is equal to the period $T_0(=2\pi/w)$ obtained when there is no resistance.

The following condition therefore is derived from the equations (22) and (23):

$$\Delta = kT = kT_0 \quad (24)$$

Since the condition of $k = 9\eta/(4a^2 p)$ is derived from the equation (11), the following condition is met:

$$\Delta = 9\eta T_0/4pa^2 \quad (25)$$

Assuming here that the mean specific weight of antibody (or antigen) is 2 kg/m³, the volume of the antibody (or antigen) having the weight of $10^{-18}$ kg is determined as $10^{-18} \text{ kg} \div 2 \text{ kg/m}^3 = 5 \times 10^{-19}$ m³. It is assumed here that the antibody (or antigen) having this volume uniformly attaches to the spherical surface of the oscillator having a radius a (spherical area being $4\pi a^2$). In such a case, the mean thickness h of the later of the antigen (or antibody) is calculated as $h = 5 \times 10^{-19}/(4\pi a^2)$m. On the other hand, since the radius a (m) of the oscillator practically ranges between $10^{-4} \geq a \geq 10^{-2}$, the following relationship (i.e. correspondence) is obtained between the radius a of the oscillator and the mean thickness h of the combinative layer:

| a(m) | mean thickness of combinative layer h(m) |
|---|---|
| $10^{-2}$ | $4 \times 10^{-16}$ |
| $10^{-3}$ | $4 \times 10^{-14}$ |
| $10^{-4}$ | $4 \times 10^{-12}$ |

A discussion will be made hereinafter as to the variation in the attenuation factor when the radius a is $10^{-4}$ while the mean thickness h is $4 \times 10^{-12}$.

It is assumed here that the condition of $9\eta T_0/(4p) = K$ (constant) is met. In such a case, the following equation is derived from the equation (25):

$$\Delta_a - \Delta_{a+h} = k/a^2 - k/(a+h)^2$$
$$= K(2ah + h^2)/(a^4 + 2a^3h + a^2h^2)$$

The term of $h^2$ is on the order of $10^{-24}$ so that it can be neglected.

The above equation therefore can be modified as follows.

$$\Delta_a - \Delta_{a+h} = K \cdot 2h/(a^3 + 2a^2h) = K \cdot 2\{(a^3/h) + 2a^2\}$$

The values of $a^3/h$ and $2a^2$ will be compared with each other, as follows:

$$a^3/h = 10^{-12}/10^{-12} = 10^0$$

$$2a^2 = 2 \times 10^{-8}$$

The term of $a^2$ can be neglected because the condition of $(a^3/h) \gg 2a^2$ is met:

$$\Delta_a - \Delta_{a+h} = K(2h/a^3)$$
$$= K \times 2 \times 4 \times 10^{-12} \times 10^{12} = 8K$$

Thus, an increment $4 \times 10^{-12}$ m causes a change of amplitude in amount of $e^{-8K}$ in each period.

It is therefore possible to conduct a quantitative analysis of the antigen (or antibody) on the order of $10^{-18}$ kg/ml, through the detection of change in the amplitude of attenuating oscillation of the oscillator.

The embodiment of the present invention will be described more practically with reference to the drawings. Referring to FIG. 1, an apparatus embodying the present invention for detecting antigen-antibody reaction has a vessel 1 for containing extracted specimen blood, detector oscillator 2 and a reference oscillator 3. The surface of the detector oscillator 2 is coated with a substance which has no substantial reactivity with the blood. An antigen (or antibody) is fixed to the coated surface of the detector oscillator 2. The surface of the reference oscillator 3 also is coated with a substance which has no substantial reactivity with the blood. The material, shape and the size of the oscillator 3 are the same as those of the detector oscillator 2.

Figure 5:
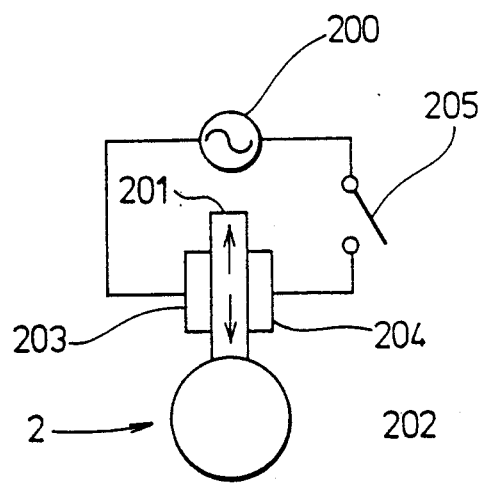
FIG. 5 is a circuit diagram showing a driving circuit for driving the oscillator of the apparatus embodying the present invention.

As more specifically shown in FIG. 5, the detector oscillator 2, as well as the reference oscillator 3, is adapted to be excited by an electric power supply 200 as is the case of ordinary quartz oscillator. The detector oscillator 2 has a rod-shaped portion 201 and a bulbous portion 202. The rod-shaped portion 201 is sandwiched between electrodes 203 and 204. As a switch is turned on, the detector oscillator 2 oscillates, i.e., moves reciprocatingly, as indicated by arrows. The power supply 200 applies electrical voltage to the electrodes 203 and 204 such that the detector oscillator 2 acts as a harmonic oscillator in the air. The circuit for driving the oscillator is omitted from FIG. 1.

Referring again to FIG. 1, an oscillator holding means 4 is designed to hold the bulbous portions 202 of the respective oscillators 2 and 3 when a predetermined amount of blood is contained in the vessel 1. Data detecting means 5 is designed to detect data concerning the amplitudes of oscillation of the oscillators 2 and 3. More specifically, the data detecting means 5 electrically collects the data concerning the amplitudes from a circuit shown in FIG. 5.

Figure 6:
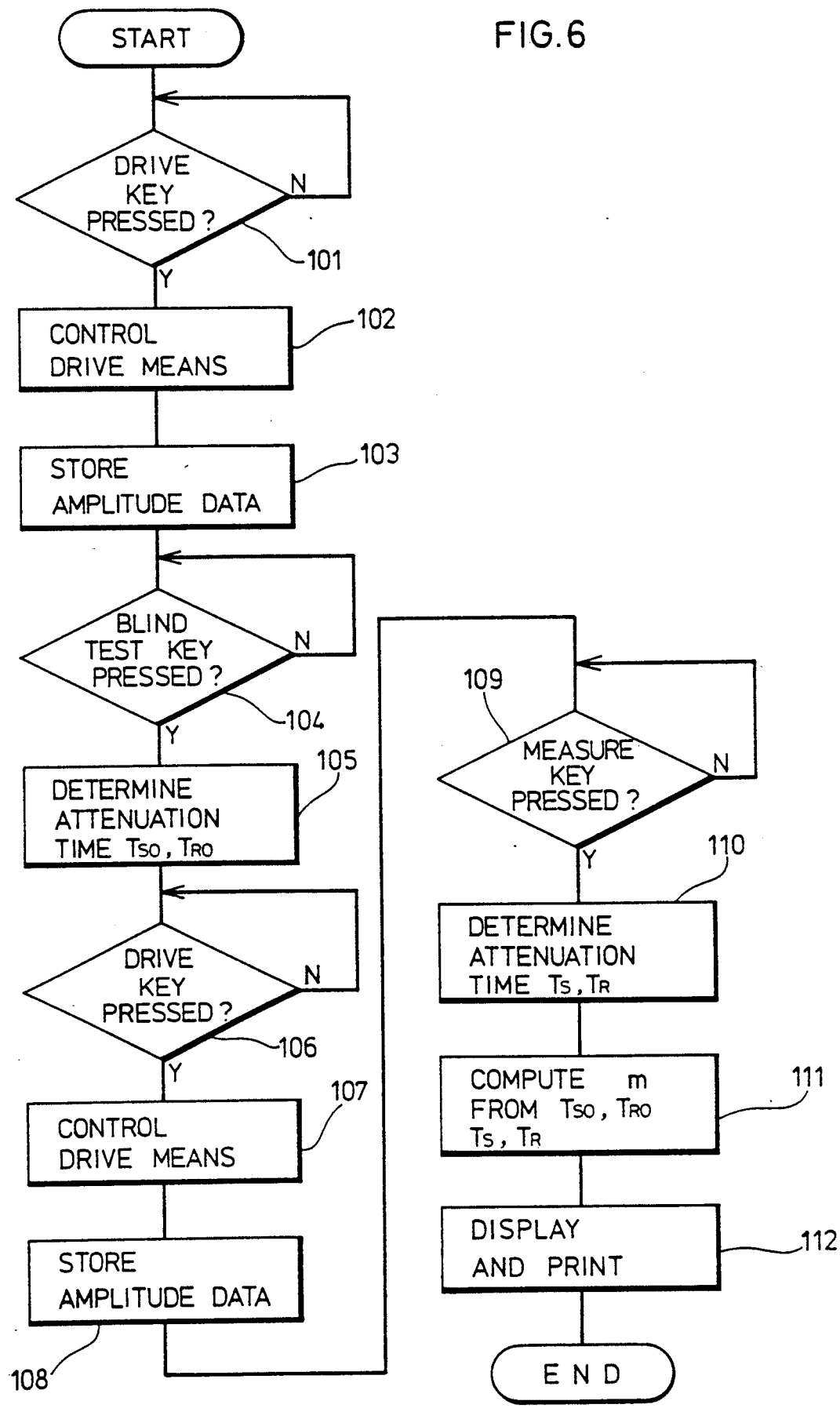
FIG. 6 is a flow chart illustrating the operation of the apparatus as shown in FIG. 1.

A control recording device 6 is capable of processing output data from the data detecting means 5 and recording the result of the processing while controlling the data detecting means 5. The control recording device 6 includes various devices such as a CPU 7 which conducts overall control of the whole apparatus, a ROM 9 and a RAM 10 which are connected to the CPU 7 through a BUS 8, an input interface 11, and output interface 12, an A/D converter 13 which conducts A/D conversion of the data output from the data detection means 5, a keyboard 14 connected to the input interface 11, a printer 15 connected to the output interface 12 and a display unit 16. The CPU 7 operates in accordance with a program stored in a ROM 9. The program stored in the ROM 9 includes a routine as shown in FIG. 6. Steps 105, 110 and 111 of the process shown in FIG. 6 correspond to the computing means which computes and determines the amount of the antibody or antigen attaching to the detector oscillator 2 as a result of the antigen-antibody reaction, whereas the printer 15 and the display device 16 correspond to the display means shown in FIG. 1 as well as Step 112 in the process of FIG. 6.

Figure 7:
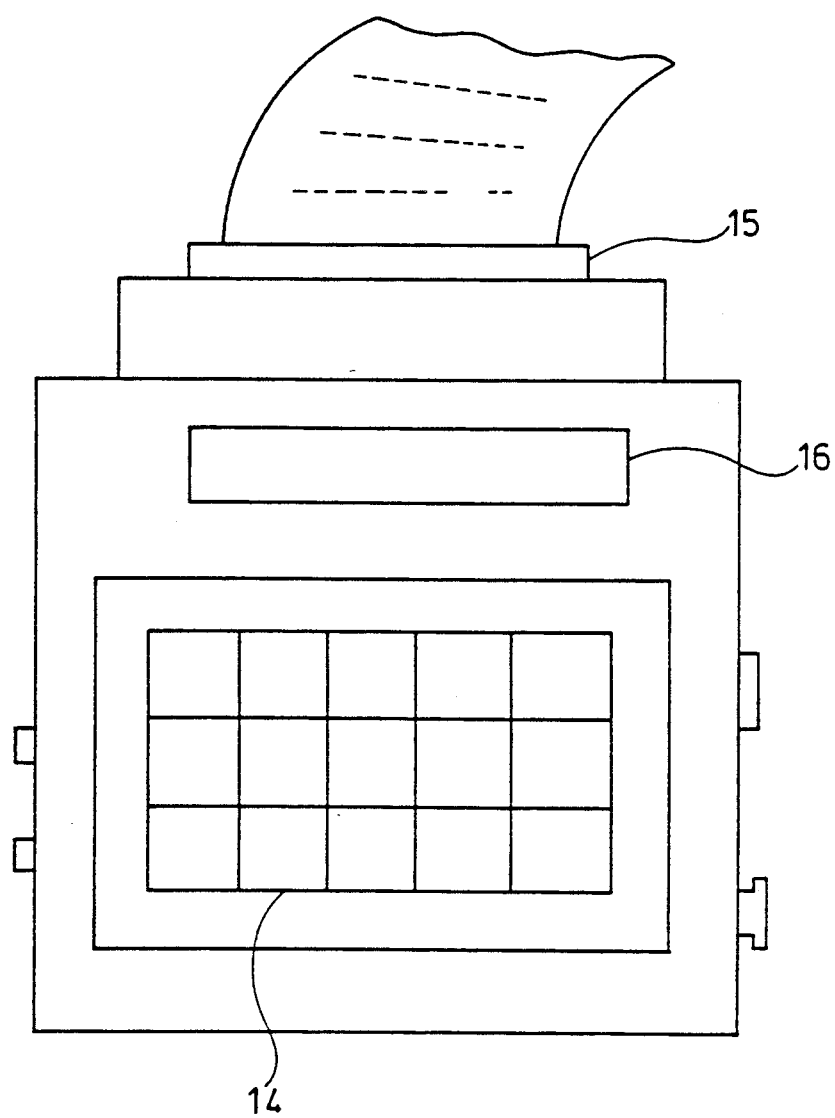
FIG. 7 shows the appearance of a control and recording apparatus as shown in FIG. 1.

FIG. 7 illustrates the appearance of the control recording device 6 of the embodiment described herein.

Figure 8:
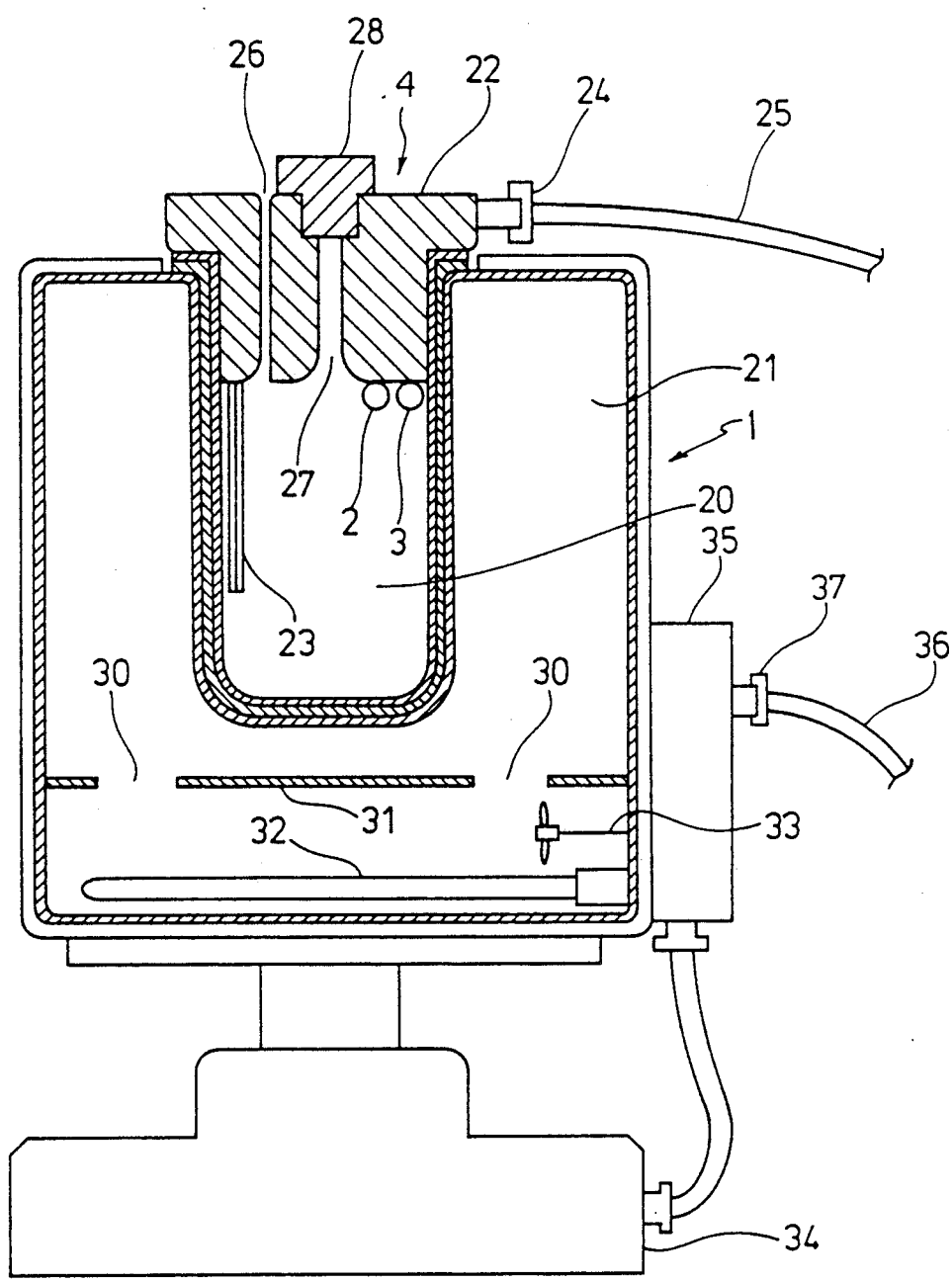
FIG. 8 shows the detail of a portion of the apparatus as shown in FIG. 1.

Referring to FIG. 8, the details of the arrangement comprising the vessel 1, oscillators 2 and 3, oscillator holding means 4, and the data detection means 5, are shown. In particular, the vessel 1 comprises an examination cell 20 and a thermostat cell 21. The opening of the examination cell 20 is closed by the holder 22. This holder 22 corresponds to the oscillator holding means 4 shown in FIG. 1. Thus, the holder 22 holds two oscillators 2 and 3 in such a manner that these oscillators 2 and 3 project inwardly from the inner surface of the holder 22.

Although not shown in FIG. 8, the data detection means 5 as shown in FIG. 1 is installed in the holder 22. In addition, the holder 22 has a sensor 23 projecting therefrom. The sensor 23 is capable of sensing the temperature and the pH value in the examination cell 20. More specifically, the sensor 23 comprises a thermistor temperature sensor, a pH detection glass, a pH detection silver electrode and a pH detection silver chloride electrode. The surface of the sensor 23 is covered by a substance which exhibits a small tendency of reaction with the blood.

The output data from the data detection means 5 and the output signal from the sensor 23 are delivered to the control recording device 6 through a connector 24 and a signal cable 25 which are provided on the holder 22. The holder 22 is further provided with an air vent hole which provides communication between the interior and exterior of the examination cell 20 and a blood injection port 27 which is adapted to be closed by a plug 28. The space in the thermostat cell 21 is divided into an upper section and a lower section by means of a partition plate 31 which is provided with a through hole 30. The lower section accommodates a heater 32 and a stirrer 33. The interior of the thermostat cell 21 is filled with a liquid which has an ability to preserve temperature, e.g., ethylene glycol.

A reference numeral 34 denotes a vibrator which is capable of vibrating the thermostat cell 21 and the examination cell 20. The heater 32, the stirrer 33 and the vibrator 34 are adapted to be vibrated by a driving means which is denoted by a numeral 35. This driving means 35 is controlled by a signal which is delivered thereto through a cable 36 and a connector 37. Although not shown, the control cable 36 is connected to an output interface 12 although such a connection is omitted from FIG. 1.

The method of the present invention will be described with reference to a flow chart shown in FIG. 6.

For the purpose of a blind test, a diluted solution having the same pH value as the specimen blood is injected through the blood injection port 27 with the plug 28 removed, until the liquid spills from the air vent hole 26. The plug 28 is then fitted to close the air vent hole 26.

Subsequently, the examiner presses a driving key on the keyboard 14. In Step 101, the CPU determines whether the driving key has been pressed. In Step 102, the CPU 7 controls the driving means 35 which is shown in FIG. 8. Namely, the CPU 7 controls the driving means 35 in accordance with the data stored in the RAM 10 and the data derived from the sensor 23, such as to drive the stirrer 33, heater 32 and the vibrator 34 in such a manner that the diluted liquid in the examination cell 20 is kept at a predetermined temperature. In Step 103, the oscillators 2 and 3 are driven to make attenuating oscillation and the data concerning the amplitude is stored in the RAM 10.

Figure 2:
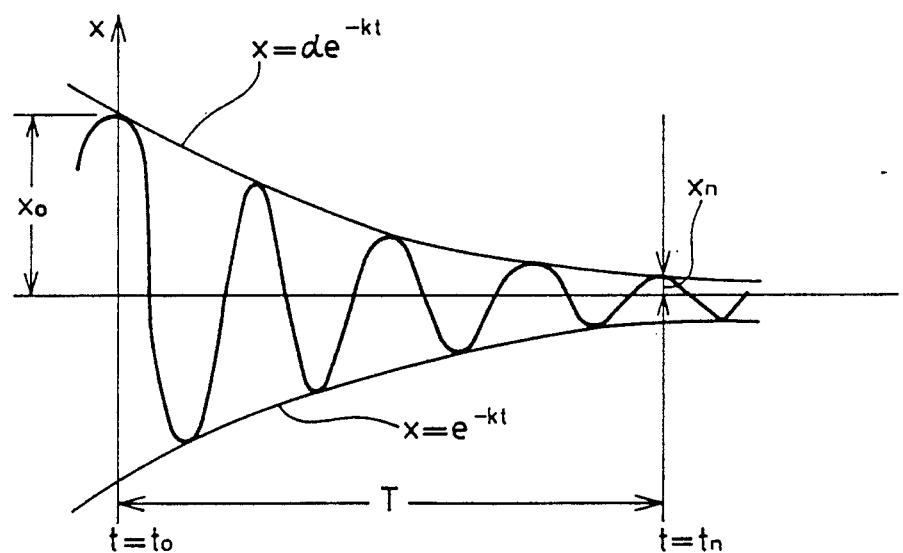
FIG. 2 is an illustration of the manner in which an oscillator incorporated in the apparatus of the present invention oscillates.

Subsequently, the examiner presses a blind test key on the keyboard 14. In Step 104 the CPU determines whether the blind test key has been pressed, and proceeds the process to Step 105 in which the CPU conducts an arithmetic computation on the basis of the amplitude data stored in the RAM 10 so as to determine the attenuation time $T_{S0}$ and $T_{R0}$ as indicated by T in FIG. 2. The attenuation time thus computed is stored in the RAM 10.

Subsequently, the examiner demounts the holder 22 from the examination cell 20 and discharges the diluted solution. The examiner then wipes off any residual solution in the cell 20 by means of a gauze and fills the examination cell 20 with the specimen blood. As in the case of the filling with the diluted solution, the examination cell is filled until the specimen blood spills over the air vent hole 26.

Subsequently, the examiner presses the above-mentioned driving key so that the CPU 7 executes Steps 106, 107 and 108 which are materially the same as Steps 101, 102, and 103 mentioned before. The examiner then presses a measuring key on the keyboard 104. In Step 109, the CPU 7 determines whether this key has been pressed and advances the process to Step 110. In Step 110, the CPU 7 conducts computation on the basis of the amplitude data stored in the RAM 10 so as to determine the attenuation time $T_S$ and $T_R$ as indicated by T in FIG. 2. The thus determined values of attenuation time are stored in the RAM 10. In Step 111, the CPU 7 performs an arithmetic operation to determine the mass $\Delta m$ of the antibody or antigen attaching to the surface of the detector oscillator 2. This arithmetic operation is conducted in accordance with the following principle. The data $T_{S0}$, $T_{R0}$, $T_S$ and $T_R$ are defined as follows:

|  | blind test | measurement |
|---|---|---|
| Attenuation time of oscillator 3 (reference oscillator) | $T_{R0}$ | $T_R$ |
| Attenuation time of oscillator 2 (detector oscillator) | $T_{S0}$ | $T_S$ |

The difference between the attenuation time as obtained with the reference oscillator 3 and that obtained with the detection oscillator 2 is expressed by $|T_R - T_S|$. This difference, which is referred to as blind error, represents the change in the attenuation time caused by the antigen-antibody reaction on both oscillators 2, 3 in the diluted solution containing blood. Since the oscillators 2 and 3 are the same as those used in the blind test, the value $T_R - T_S$ is understood to contain no component corresponding to the value $|T_{R0} - T_{S0}|$. Therefore, the variation $\Delta T$ of the attenuation time attributable solely to the antigen-antibody reaction, is given by the following equation:

$$\Delta T = |T_R - T_S| - |T_{R0} - T_{S0}| \quad (26)$$

It is conceivable that some components of the blood attach to the oscillators 2 and 3 due to action other than the antigen-antibody reaction, e.g., adsorption. Such effect, however, it considered to occur equally both on $T_R$ and $T_S$. The influence of such effect, therefore, can be eliminated by the subtraction of $|T_R - T_S|$.

As explained before in connection with the equation (12), the following relationship exists between the radius a of the oscillator and the attenuation time T:

$$T = C \cdot a^2 \quad (27)$$

where C represents a constant.

The radius of the detector oscillator 2 without any matter attaching thereto is represented by $a_0$, while the radius of the same with antibody or antigen attaching to the surface thereof, is represented by $a_S$. Then, the following relationships are derived from the equation (27):

$$T_0 = C \cdot a_0^2 \quad (28)$$

$$T_0 + \Delta T = C \cdot a_S^2 \quad (29)$$

where, $T_0$ represents the attenuation time of the naked detector oscillator 2.

Then, the following relationship is obtained by subtracting both sides of the equations (28) and (29):

$$\Delta T = C(a_S^2 - a_0^2) \quad (30)$$

The increment amount $\Delta T$ can be determined through measurement, and since $a_0$ is known, the value $a_S$ can be determined from the equation (30).

The volume of the matter attaching to the detector oscillator 2, therefore, can be determined in the same manner as the equation (14) as follows:

$$\Delta V = 4/3(a_S^3 - a_0^3) \quad (31)$$

The mass m can be determined in the manner explained in connection with the equation (15) as follows:

$$\Delta m = 4/3(a_S^3 - a_0^3) \quad (32)$$

The CPU 7 then executes Step 112 in which the mass m is displayed on the display device 16 and then activates the printer 15 thereby to print out the displayed data. The described embodiment minimized the measurement error by virtue of the use of the reference oscillator so that a high degree of accuracy of measurement can be assured. A further improvement in the measuring accuracy is obtained by effecting a correction on the mass m determined by the equation (32) in accordance with the temperature and the pH value as obtained through the sensor 23.

Although the oscillators 2 and 3 in the described embodiment have bulbous form, this is only illustrative and the oscillators can have various forms such as cylindrical form, conical form, pyramidal form, polygonal form and so forth, as well as a combination of such forms. The material of the oscillators 2 and 3 also have wide selection. Namely, the oscillators 2 and 3 may be made of a semiconductor (organic or inorganic), quartz, rock-forming mineral, glass, artificial mineral, synthetic resin and ceramics. Furthermore, the examination cell 20 can have a variety of internal configurations such as cylindrical, polygonal, conical and pyramidal configurations.

While the particular embodiments shown and described above have proven to be useful in many applications involving the above-mentioned art, further modifications herein disclosed will occur to persons skilled in the art to which the present invention pertains and also such modifications are deemed to be within the scope and spirit of the present invention defined by the appended claims.

What is claimed is:

1. A method for measuring the quantity of the product of an antigen-antibody reaction, which comprises the steps of:

fixing one of a predetermined antigen and a predetermined antibody to an oscillatable detection body;

immersing the detection body and an oscillatable reference body in a specimen having one of an antibody and an antigen reactable with the other of the antigen and the antibody fixed to the detection body, the reference body having substantially the same dimensions and being formed of the same material as the detection body, and having no antigen and antibody fixed thereto so as to bind the antibody or antigen in the specimen to the antigen or antibody fixed to the detection body;

exciting the detection body and the reference body to cause the detection body and reference body to oscillate;

measuring the time $T_S$ taken for oscillations of the detection body to decrease in amplitude from a first initial oscillation amplitude to a predetermined second oscillation amplitude;

measuring the time $T_R$ taken for oscillations of the reference body to decrease in amplitude from a third initial oscillation amplitude to a predetermined fourth oscillation amplitude; and determining the quantity of one of the antigen and antibody of the specimen reacting to the other of the antibody and antigen fixed to the detection body, the quantity being proportional to the difference between time $T_R$ and time $T_S$.

2. A method as defined by claim 1, wherein the specimen is blood.

3. A method for measuring the quantity of the product of an antigen-antibody reaction, which comprises the steps of:

fixing one of a predetermined antigen and a predetermined antibody to an oscillatable detection body;

immersing the detection body in a specimen having one of an antibody and an antigen reactable with the other of the antigen and the antibody fixed to the detection body so as to bind the antibody or antigen in the specimen to the antigen or antibody fixed to the detection body;

exciting the detection body to cause the detection body to oscillate;

measuring the time $T_S$ taken for oscillations of the detection body to decrease in amplitude from a first initial oscillation amplitude to a predetermined second oscillation amplitude; and determining the quantity of one of the antigen and antibody of the specimen reacting to the other of the antibody and antigen fixed to the detection body, the quantity being proportional to the time $T_S$.

4. A method as defined by claim 3, wherein the specimen is blood.

5. Apparatus for measuring the quantity of the product of an antigen-antibody reaction, which comprises:

a vessel for containing a specimen, the specimen containing one of an antigen and an antibody;

an oscillatable detection body, the oscillatable detection body having fixed thereon one of an antibody and an antigen reactable with the other of the antigen and antibody contained in the specimen, the oscillatable detection body being immersable in the specimen to allow the one of the antigen and the antibody contained in the specimen to react with the other of the antibody and antigen fixed to the detection body;

an oscillatable reference body, the oscillatable reference body having no antibody and antigen fixed thereon, the oscillatable reference body being immersable in the specimen;

means operatively coupled to the detection body and the reference body for detecting the amplitude of the oscillations of the detection body and the reference body, the oscillation amplitude detection means providing output data representative of the oscillation amplitude of the detection and reference bodies;

means for processing the output data from the oscillation amplitude detection means and for measuring the time $T_S$ taken for oscillations of the detection body to decrease in amplitude from a first initial oscillation amplitude to a predetermined second oscillation amplitude, and for measuring the time $T_R$ taken for oscillations of the reference body to decrease in amplitude from a third initial oscillation amplitude to a predetermined fourth oscillation amplitude, the processing means further determining the quantity of one of the antigen and antibody contained in the specimen reacting to the other of the antibody and antigen fixed to the detection body, the quantity being proportional to the difference between time $T_R$ and time $T_S$; and display means operatively coupled to the processing means for displaying the quantity determination.

6. Apparatus for measuring the quantity of the product of an antigen-antibody reaction, which comprises:

a vessel for containing a specimen, the specimen containing one of an antigen and an antibody;

an oscillatable detection body, the oscillatable detection body having fixed thereon one of an antibody and an antigen reactable with the other of the antigen and antibody contained in the specimen, the oscillatable detection body being immersable in the specimen to allow the one of the antigen and antibody contained in the specimen to react with the other of the antibody and antigen, fixed to the detection body;

means operatively coupled to the detection body for detecting the amplitude of the oscillations of the detection body, the oscillation amplitude detection means providing output data representative of the oscillation amplitude of the detection body; and means for processing the output data from the oscillation amplitude detection means and for measuring the time $T_S$ taken for oscillations of the detection body to decrease in amplitude from a first initial oscillation amplitude to a predetermined second oscillation amplitude, the processing means further determining the quantity of one of the antigen and antibody contained in the specimen reacting to the other of the antibody and antigen fixed to the detection body, the quantity being proportional to the time $T_S$; and display means operatively coupled to the processing means for displaying the quantity determination.

* * * * *